United States Patent [19]

Hussein

[11] 4,275,730

[45] Jun. 30, 1981

[54] SYRINGE WITH PRESSURE-LIMITED DELIVERY

[75] Inventor: Hany M. Hussein, Clifton, N.J.

[73] Assignee: Becton, Dickinson and Company, Paramus, N.J.

[21] Appl. No.: 91,323

[22] Filed: Nov. 5, 1979

[51] Int. Cl.³ .............................................. A61M 1/00
[52] U.S. Cl. .................................... 128/234; 128/215
[58] Field of Search ........ 128/218 R, 218 C, 218 PA, 128/218 P, 234, 215

[56] References Cited

U.S. PATENT DOCUMENTS 3,978,846  9/1976  Bailey .......................... 128/218 C X

FOREIGN PATENT DOCUMENTS 414253  10/1910  France .................................... 128/234
19902    2/1896  United Kingdom ..................... 128/234

Primary Examiner—John D. Yasko
Attorney, Agent, or Firm—Richard J. Rodrick

[57] ABSTRACT

A syringe with pressure-limited delivery capacity includes a barrel having a chamber for retaining fluid and a passageway through the distal end of the barrel communicating with the chamber for delivering fluid to a fluid receiving device. A plunger is slidably positioned in fluid-tight engagement inside the barrel and is adapted to force fluid from the chamber through the passageway upon its distally directed movement. A hollow fluid by-pass is connected to the barrel near its distal end with the lumen of the by-pass communicating with the chamber in a permanently open condition. The opposite end of the by-pass is adapted to vent to atmospheric pressure level conditions. The flow resistance of the by-pass is selected so as to pre-determine the pressure level inside the chamber required for fluid to flow out of the opposite end of the by-pass upon distal movement of the plunger.

6 Claims, 4 Drawing Figures

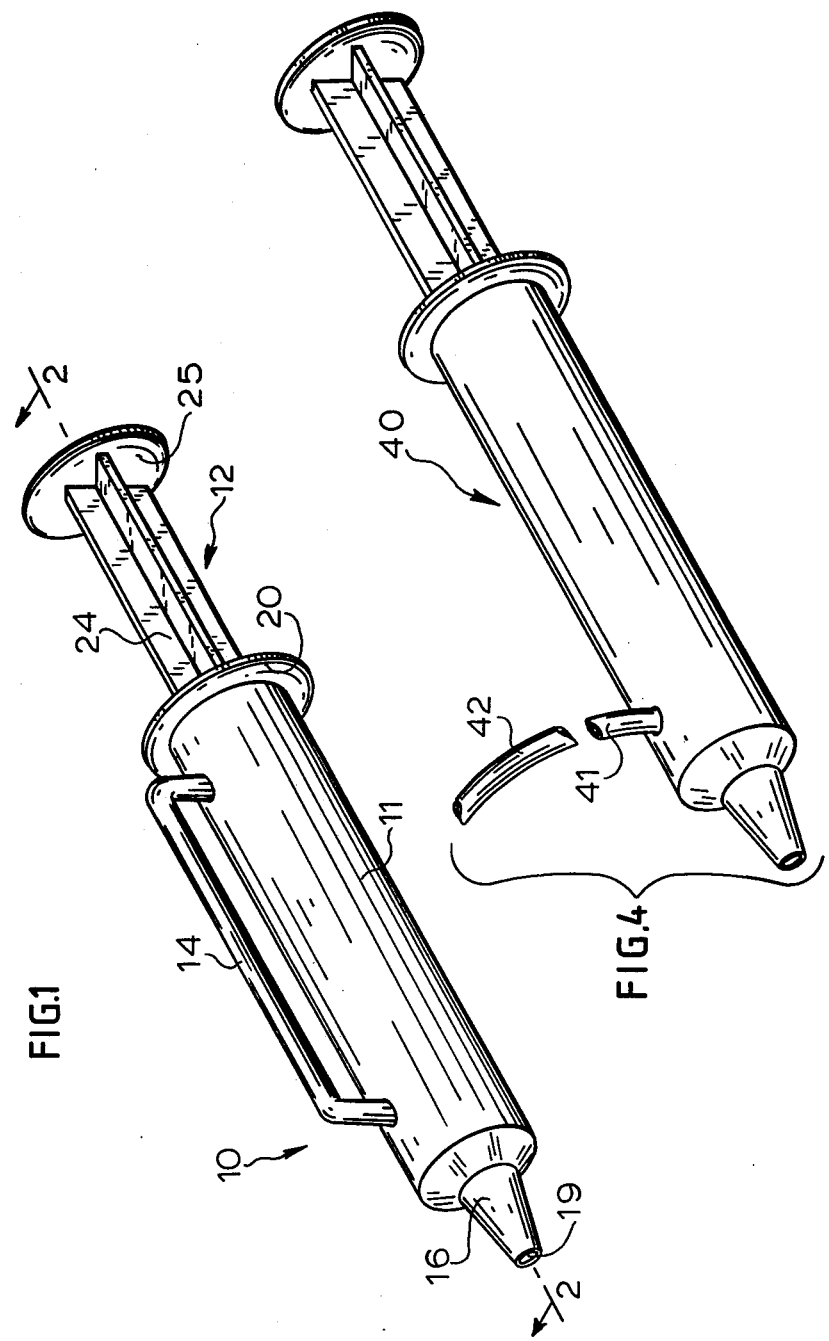

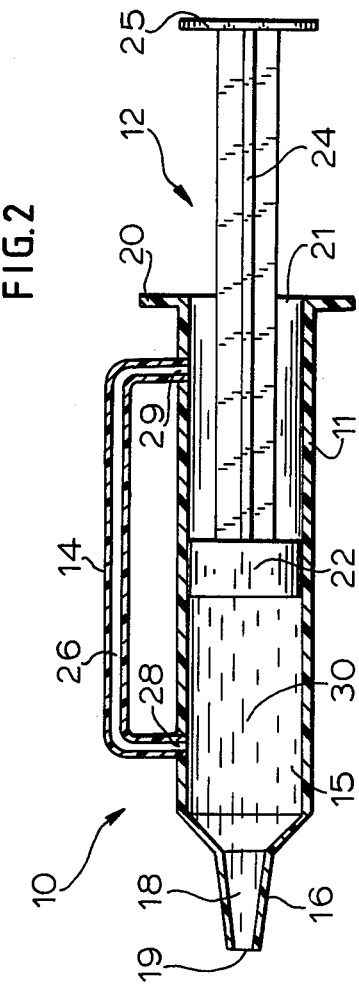
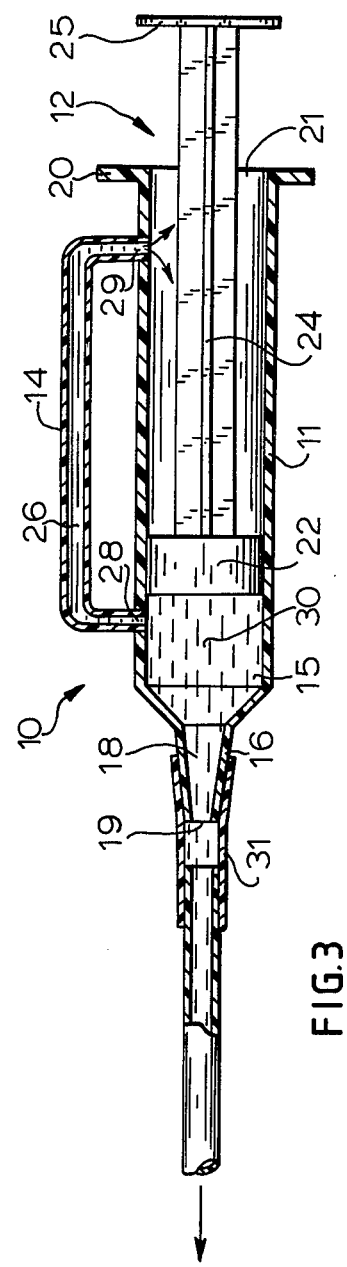

SYRINGE WITH PRESSURE-LIMITED DELIVERY

BACKGROUND OF THE INVENTION

The present invention relates to a syringe useful for delivering fluid to a fluid receiving device such as a balloon catheter, and more particularly, concerns a syringe for such use with pressure-limited delivery capacity.

Syringes are commonly utilized by physicians, surgeons and other medical personnel for a variety of situations involving the delivery of fluid. One particular situation involves the inflation of a balloon catheter which is intended to be positioned inside a blood vessel of a patient, and then inflated to a sufficient degree to occlude the path of the blood vessel. This balloon catheter is generally injected with a fluid through an insertion tube or catheter by means of a syringe inserted in and connected to the end of the tube which may extend outside of the patient. However, inasmuch as the balloon portion of the catheter is confined within the blood vessel of the patient, inflating the same can oftentimes be a matter of guesswork since the balloon cannot be seen by the operator during its inflation. It can be appreciated that, without proper controls or monitoring means, such a balloon catheter can easily be underinflated or overinflated. Underinflation of a balloon catheter inside the blood vessel will result in a loose fit therewithin so that the balloon itself is not snugly confined against the walls of the blood vessel. With this condition, the balloon is prone to migration within the blood vessel, which is clearly undersirable. On the other hand, overinflation of the balloon may result in its rupture during inflation or may result in a condition of being overstressed so that premature failure of the balloon while in the blood vessel may occur. This condition also is undesirable. Accordingly, the filling of a fluid receiving device, particularly a fluid-sensitive balloon catheter, by a syringe can be problematical without a control or monitoring mechanism to assist the operator in determining the proper amount of fluid for optimum inflation of the fluid receiving device.

There have been attempts to rectify this deficiency, particularly in the inflation of balloon catheters, by the utilization of various control devices. For instance, U.S. Pat. Nos. 4,147,170; 4,116,201 and 3,799,171 all disclose devices for controlling the inflation of balloon catheters. However, the devices disclosed in these patents all rely upon a valve or valving mechanism to open and close at the appropriate pressure levels for controlling the amount of fluid to be delivered to the balloon catheter. Another patent, namely U.S. Pat. No. 4,000,741, discloses a syringe useful for pumping fluid into a body cavity of a patient or into a fluid receiving device, which relies upon a flexible balloon secured to an extension member at the tip of the syringe. This balloon inflates at a pre-determined pressure level to relieve pressure generated by the syringe so as to control the level of pressure being pumped into the fluid receiving device. The devices described in conjunction with the aforementioned patents, while attempting to resolve the need to control the inflation pressure into the balloon catheter, oftentimes involve somewhat complex structure in their manufacture with resultant increase in production cost and quality control procedures. Moreover, use of valving mechanisms and inflatable balloons at the tip of the syringe adds another element to the structure of this type device with the concomitant risk that such an additional element may fail during use to the detriment of the patient. Accordingly, simplified improvements in a syringe for controlling the amount of fluid for delivery to a fluid receiving device are still being sought. The present invention is directed to that end, and satisfies the need for such a syringe with a pressure controlling provision.

SUMMARY OF THE INVENTION

A syringe with pressure-limited delivery capacity comprises a barrel having a chamber for retaining fluid and a passageway through the distal end of the barrel communicating with the chamber for delivering fluid to a fluid receiving device. Plunger means is slidably positioned in fluid-tight engagement inside the barrel and is adapted to force fluid from the chamber through the passageway upon its distally directed movement. Hollow fluid by-pass means is connected to the barrel near its distal end with the lumen of the by-pass means communicating with the chamber in a permanently open condition. The opposite end of the by-pass means is adapted to vent to atmospheric pressure level conditions. The flow resistance parameters of the by-pass means are selected so as to pre-determine the pressure level inside the chamber required for fluid to flow out of the opposite end of the by-pass means upon distal movement of the plunger means. This pressure level is thus the maximum pressure level which the syringe is capable of delivering to the fluid receiving device.

In one embodiment of the present invention, the by-pass means is a length of hollow tubing, one end of which is connected to the barrel near its distal end, the opposite end of which is connected to the barrel proximally from the fluid-tight plunger in a region therein of atmospheric pressure conditions so that fluid can be vented back into the barrel of the syringe. This provides a neater package for the syringe and by-pass tubing combination. Moreover, another feature of the present invention allows the length of the by-pass tubing to be adjustable to vary the maximum pressure the syringe is capable of delivering to the fluid receiving device.

From the structural standpoint, the pressure-limited syringe of the present invention is notably different from prior art syringes useful for inflating balloon catheters. In particular, the by-pass tubing always remains in an open condition, thereby eliminating the need for valving mechanisms or additional balloon expanding devices. This significantly simplifies the structure of the syringe over other syringe devices useful for inflating balloon catheters. Furthermore, inasmuch as the present invention relies upon the fundamental relationship between the flow resistance of the tube, the flow through the tube and the pressure differential across the tube, the present device can be calibrated in a pre-determined fashion to allow inflation of a balloon catheter only to a controlled pressure. However, the maximum delivery pressure can be varied by changing the length of the by-pass tubing, one of the flow-resistance parameters which this invention relies upon for operation. In addition, operation of this improved, pressure-limited syringe relies upon only forward motion of the plunger inside the barrel of the syringe. Forward motion of the plunger inflates the balloon to the desired pressure and then automatically stops inflating the balloon when the maximum pressure has been reached and fluid starts flowing out of the by-pass element. Thus, the need for reversing the direction of motion of the plunger and for observing volume control as in some prior syringes has been eliminated. Other advantages of the present invention are offered as well.

BRIEF DESCRIPTION OF THE DRAWINGS

FIG. 1 is a perspective view of the preferred syringe with pressure-limited delivery capacity of the present invention;

FIG. 2 is a cross-sectional view taken along line 2—2 of FIG. 1 illustrating the contents of the syringe before fluid is delivered to a fluid receiving device;

FIG. 3 is a cross-sectional view similar to FIG. 2 illustrating the syringe connected to a fluid receiving device with the pressure-limited by-pass tubing performing its pressure control feature; and FIG. 4 is a perspective view of a syringe with pressure-limited delivery capacity with an alternate construction of the by-pass tubing.

DETAILED DESCRIPTION

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment or embodiments illustrated. The scope of the invention will be pointed out in the appended claims.

Adverting to the drawings, particularly FIGS. 1 and 2, there is illustrated the preferred embodiment of a syringe 10 with pressure-limited delivery capacity. Syringe 10 includes three general components: an elongate, substantially cylindrical barrel 11, a plunger assembly 12 and a length of hollow by-pass tubing 14.

Cylindrical barrel 11 includes a chamber 15 which is adapted to retain a fluid which is eventually going to be devlivered to a fluid receiving device. At its distal end, barrel 11 is preferably formed to include a tapered portion 16 to facilitate the connection of the syringe to the appropriate fluid receiving device. A passageway 18 extends through tapered portion 16 at the distal end of the barrel terminating in an opening 19 on one end and communicating with chamber 15 on the other end so that fluid in chamber 15 can pass through passageway 18 for delivery to the fluid receiving device. A flange 20 is positioned at the proximal end of barrel 11 to facilitate a grip by the user during operation. Chamber 15 terminates in a large opening 21 at the proximal end of the barrel sufficient to accommodate plunger assembly 12.

Plunger assembly 12 includes a plunger 22 generally sized to slidably fit in fluid-tight engagement inside barrel 11. The fluid-tight engagement of the plunger to the inside wall of the barrel will assure that any fluid particularly in the distal portion of the barrel, will be effectively forced out passageway 18 during the operation of this syringe. An extension member 24 is connected to plunger 22 and extends sufficiently outwardly from the barrel to facilitate its operation by the user. A disk 25 or the like is at the opposite end of extension member 24 to provide a convenient pushing surface for the thumb of the user. While plunger 22 is preferably cylindrically shaped to mate with the inside wall of the barrel, extension member 24 may be configured in a variety of shapes as long as it has sufficient strength to maintain its rigidity during movement of the plunger assembly inwardly.

By-pass tubing 14 is connected at one end to barrel 11 near the distal end of the barrel, with the hollow lumen 26 of the tubing communicating with chamber 15. It is to be noted that the entrance 28 of tubing 14 is in a permanently open condition, there being no valves or other devices to operatively open and close this entrance. Accordingly, fluid in chamber 15 is always free to flow through entrance 28 into the lumen of the by-pass tubing, depending, of course, on the pressure levels of the fluid in the chamber and the flow resistance of the by-pass tubing. Opposite end 29 of the by-pass tubing, in this preferable embodiment, is also connected to barrel 11, but proximally from the location of plunger 22 in its normal operating position inside the barrel. It can be seen, then, that end 29 of the by-pass tubing is maintained at normal atmospheric pressure conditions inasmuch as the proximal portion of the barrel is open to the atmosphere. In the embodiment being described, end 29 is so connected to the barrel in order to provide a neater package and one in which by-pass tubing 14 is maintained in a controllably fixed position. Thus, this structure allows fluid from the distal portion of the barrel under appropriate pressure conditions to be vented back into the proximal end of the barrel which is at atmospheric pressure conditions.

As alluded to above, inasmuch as the principle of operation of the by-pass tubing utilizes the fundamental relationship between the flow resistance of a tube, flow through the tube and the pressure differential across the tube, the diameter and the length of the tubing can be selected so as to pre-determine the pressure level inside the chamber required for fluid to flow out of opposite end 29 of by-pass tubing 14 upon distal movement of the plunger. For convenience purposes, the inside diameter of the by-pass tubing and entrance 29 therein, being generally of a very small diameter, usually remain fixed without variation; thus, the length of the by-pass tubing is generally the characteristic which is varied in order to adjust the pressure level inside the chamber for fluid to flow out of the opposite end of the tubing. With an appropriate fluid 30, such as a radiopaque dye, placed in the distal portion of chamber 15, the syringe of the present invention is ready for operation.

Referring now to FIG. 3, tapered portion 16 is mated with an appropriate connector 31 which leads to a fluid receiving device, such as a balloon catheter (not shown). Such a balloon catheter device is generally a fluid-tight receptacle into which fluid is delivered in order to inflate same. As can be seen in FIG. 3, plunger assembly 12 has been moved in a distal direction thereby forcing fluid 30 through passageway 18 and on into the fluid receiving device. Concurrent with this distal movement of the plunger assembly, the pressure level inside the distal portion of chamber 15 rises. This pressure level in the chamber will be substantially the same as the pressure level inside the fluid receiving device, since that device is a closed pressure system. When the pressure level inside the chamber rises, fluid is allowed to flow through entrance 28 into the lumen of the by-pass tubing. As the pressure level increases, the fluid distance or height inside by-pass tubing also increases. This increase continues until the operator observes fluid flowing out of opposite end 29 of the tubing back into the proximal end of the barrel. When fluid flows back into the barrel, the maximum pressure level inside the distal portion of the barrel has been reached, this pressure level being the maximum pressure that the syringe is capable of delivering to the fluid receiving device. This pressure level is known to the operator beforehand, since the flow characteristics of the by-pass tubing allow the operator to calibrate the maximum pressure which can be reached before fluid flows out of the by-pass tubing. Therefore, without the use of valves or other operative elements in the syringe, an effective control over the pressure level inside the fluid receiving device is achieved.

Turning now to FIG. 4, a syringe 40 is illustrated having similar components as the syringe described in conjunction with FIGS. 1 through 3. However, by-pass tubing 41 is connected only to the barrel near its distal end, with opposite end 42 of the by-pass tubing remaining free of any connection so that it is adapted to vent to atmospheric pressure level conditions. With the use of flexible tubing in this embodiment, it is possible to develop high pressure levels inside the chamber before the by-pass tubing feature comes into effect. This is accomplished by significantly increasing the length of by-pass tubing 41 and merely wrapping same around the periphery of the substantially cylindrical barrel of the syringe. For example, when utilizing tubing with an inside diameter of 0.012 inches (0.0305 cm.), it is possible to inflate a balloon catheter in an artery up to 400 mmHg by providing a tubing length of about 12 inches (30.5 cm.). Since such a tubing length could be unwieldy, wrapping same around the barrel of the syringe will conveniently and neatly keep the tubing in a manageable position. When the pre-determined pressure level inside the balloon catheter is reached, fluid will flow out of the by-pass tubing thereby indicating to the operator that the maximum pressure level has been attained.

Thus, the syringe of the present invention provides a controllable, preferably adjustable or variable, pressure-limited delivery capacity feature in the fluid filling of such devices as balloon catheters. Its simplified structure makes this invention efficient, straight-forward in its use and operation and effective in its results.

What is claimed is:

1. A syringe with pressure-limited delivery capacity comprising:
   an elongate barrel having a chamber for retaining fluid;
   a passageway through the distal end of said barrel communicating with said chamber for delivering said fluid to a fluid receiving device;
   a plunger slidably positioned in fluid-tight engagement inside said barrel having one end extending outwardly from said barrel to facilitate its operation, said plunger adapted to force fluid from said chamber through said passageway upon its movement toward said distal end; and
   a length of hollow by-pass tubing connected to said barrel near its distal end, the hollow lumen of said tubing communicating with said chamber in a permanently open valveless condition, the opposite end of said tubing adapted to vent to atmospheric pressure level conditions, the diameter and the length of said tubing selected so as to pre-determine the pressure level inside said chamber required for fluid to flow out of the opposite end of said tubing upon distal movement of said plunger, said pressure level thereby being the maximum pressure level which said syringe is capable of delivering to said fluid receiving device.

2. The syringe of claim 1 wherein said barrel and said plunger are cylindrically shaped.

3. The syringe of claim 1 wherein said opposite end of the by-pass tubing is connected to said barrel proximally from said fluid-tight plunger in a region therein of atmospheric pressure conditions so that fluid can be vented back into the barrel of the syringe.

4. The syringe of claim 1 wherein the length of said by-pass tubing is adjustable to vary the maximum pressure the syringe is capable of delivering to said fluid receiving device.

5. A syringe with pressure-limited delivery capacity comprising:
   a barrel having a chamber for retaining fluid;
   a passageway through the distal end of said barrel communicating with said chamber for delivering said fluid to a fluid receiving device;
   plunger means slidably positioned in fluid-tight engagement inside said barrel adapted to force fluid from said chamber through said passageway upon its distally directed movement; and
   hollow fluid by-pass means connected to said barrel near its distal end, the lumen of said by-pass means communicating with said chamber in a permanently open valveless condition, the opposite end of said by-pass means adapted to vent to atmospheric pressure level conditions, the flow resistance characteristics of said by-pass means being selected so as to pre-determine the pressure level inside said chamber required for fluid to flow out of the opposite end of said by-pass means upon distal movement of said plunger means, said pressure level thereby being the maximum pressure level which said syringe is capable of delivering to said fluid receiving device.

6. A syringe with pressure-limited delivery capacity comprising:
   an elongate, substantially cylindrical barrel having a chamber for retaining fluid;
   a passageway through the distal end of said barrel communicating with said chamber for delivering said fluid to a fluid receiving device;
   a substantially cylindrical plunger slidably positioned in fluid-tight engagement inside said barrel having one end extending outwardly from said barrel to facilitate its operation, said plunger adapted to force fluid from said chamber through said passageway upon its movement toward said distal end; and
   a length of hollow by-pass tubing connected to said barrel near its distal end, the hollow lumen of said tubing communicating with said chamber in a permanently open valveless condition, the opposite end of said tubing being connected to said barrel proximally from said fluid-tight plunger in a region therein of atmospheric pressure conditions so that fluid can be vented back into the barrel of the syringe, the diameter and the length of said tubing being selected so as to pre-determine the pressure level inside said chamber required for fluid to flow out of the opposite end of said tubing upon distal movement of said plunger, said pressure level thereby being the maximum pressure level which said syringe is capable of delivering to said fluid receiving device, the length of said by-pass tubing being adjustable to vary said maximum pressure the syringe is capable of delivering.

* * * * *